United States Patent
Isozaki

[11] Patent Number: 5,814,828
[45] Date of Patent: Sep. 29, 1998

[54] APPARATUS FOR DEFINING THE LOCATION OF A FOREIGN OBJECT ON A ROTARY BODY IN TERMS OF A COORDINATE SYSTEM

[75] Inventor: Hisashi Isozaki, Tokyo, Japan

[73] Assignee: Kabushiki Kaisha Topcon, Tokyo, Japan

[21] Appl. No.: 538,821

[22] Filed: Oct. 5, 1995

[30] Foreign Application Priority Data

Oct. 7, 1994 [JP] Japan .................................. 6-244260

[51] Int. Cl.⁶ .................................................. G01N 21/88
[52] U.S. Cl. ..................... 250/559.41; 356/237
[58] Field of Search .................. 250/559.41; 356/430, 356/431, 237

[56] References Cited

U.S. PATENT DOCUMENTS 5,377,002 12/1994 Malin et al. ............................ 356/237

FOREIGN PATENT DOCUMENTS 57-108606  7/1982  Japan .
60-15939   1/1985  Japan .
3-75055   11/1991  Japan .

Primary Examiner—Edward P. Westin
Assistant Examiner—Kevin Pyo
Attorney, Agent, or Firm—Reid & Priest L.L.P.

[57] ABSTRACT

An apparatus for determining the location of a foreign object on a rotary body rotates the body around a horizontally-movable vertical axis. A horizontal displacement detector detects the horizontal displacement of the axis and provides a first signal representing that displacement. An angular position detector detects the angular position of the body and provides a second signal representing that angular position. A lighting system illuminates the body's surface, and a light receiving system receives light that is reflected from the surface. A maximum value of an output signal of the light receiving system is determined to correspond to a representative value of angular position. A position determining section determines the position of the representative value based on the first signal representing the horizontal displacement, the second signal representing angular position, and a clock signal. A foreign object detecting section determines that a representative value exceeding a predetermined level to corresponds to a foreign object.

2 Claims, 5 Drawing Sheets

APPARATUS FOR DEFINING THE LOCATION OF A FOREIGN OBJECT ON A ROTARY BODY IN TERMS OF A COORDINATE SYSTEM

[FIELD OF THE INVENTION]

This invention relates to an apparatus for defining the location of a foreign object on a rotary body in terms of a coordinate system and, more particularly, it relates to an apparatus adapted to accurately define the location of a particle such as a dust particle found on a rotating wafer in terms of a coordinate system and efficiently observe it through an electronic microscope with a very narrow field of vision in order to appropriately handle it.

[DESCRIPTION OF THE RELATED ART]

Known examples of apparatus of a first category for defining the location of a particles on a wafer in terms of a coordinate system include a foreign object screening apparatus disclosed in Japanese Patent Publication No. 60-15939 and an automatic appearance examining apparatus disclosed in Japanese Patent Publication No. 57-108606. With any of these apparatuses, a wafer placed on a moving mount is moved and screened for foreign objects through a high magnification microscope or a photoelectric detector and the location of each of the detected foreign objects is defined in terms of a coordinate system by determining the amount of displacement from a reference point typically by means of an encoder.

Known examples of apparatus of a second category for defining the location of a particle on a wafer in terms of a coordinate system include an arrangement with which the upper surface of a wafer is divided into rectangularly parallelepipedic pixels, each having a predetermined surface area, the quantity of scattering light of each of the pixels is measured, and if the quantity of scattering light of any of the pixels exceeds a predetermined level, it is determined to have a particle thereon so that the location of the pixel is detected and stored in a memory in terms of a coordinate system.

With an apparatus of the first category for defining the location of a particle on a wafer in terms of a coordinate system, the location of the particle defined in terms of a coordinate system corresponds to a set of data for representing the detected pixel, which occupies an area of a rotary body. In other words, the accuracy with which the location is defined is inherently limited by the size of the pixels of the rotary body.

On the other hand, with an apparatus of the second category, the accuracy with which the location of a detected particle on a wafer (the spatial resolution) is defined is also inherently limited by the surface area of the pixel carrying the particle and, therefore, the apparatus is not adapted for high precision measurements requiring the use of an analyzing device such as an electronic microscope.

SUMMARY OF THE INVENTION

In view of the above identified problems and other problems of conventional apparatuses for defining the location of a foreign object on a rotary body in terms of a coordinate system, it is therefore an object of the present invention to provide a novel apparatus of the type under consideration that has a simple configuration but can precisely define the location of a foreign object on a rotary body in terms of a coordinate system.

It is another object of the present invention to provide an apparatus for defining the location of a foreign object on a rotary body in terms of a coordinate system having an angular resolution for detecting a small angle that exceeds the angular resolution of an ordinary encoder for detecting a small angle.

It is still another object of the present invention to provide an apparatus for defining the location of a foreign object on a rotary body in terms of a coordinate system that can highly precisely detect the angular position of an object for each sector to be examined without accumulating timing errors of clock pulse in an angular position detecting device such as an encoder of the apparatus.

According to the present invention, the above objects are achieved by providing an apparatus for defining a location of a foreign object on a rotary body in terms of a coordinate system, the rotary body adapted to rotate around a horizontally-movable vertical axis of rotation. The apparatus has a horizontal displacement detector that detects a horizontal displacement of the vertical axis and transmits a first signal representing the horizontal displacement, and an angular position detector detects an angular position of the rotary body and provides a second signal representing the angular position. A lighting optical device illuminates the rotary body's surface, and a light receiving portion receives light that is reflected by the rotary body's surface and produces a third signal representing reflected light. Another portion is responsive to the second signal representing the angular position, and determines that a maximum value of the third signal from the lighting receiving portion corresponds to a representative value of angular position. A position determining portion determines a position corresponding to the representative value, based on the first signal representing the horizontal displacement, the second signal representing the angular position, and a clock signal. Finally, a foreign object detecting portion determines that a representative value exceeding a predetermined level corresponds to the foreign object.

If said rotary body rotates at a rate of M rotations per second and said angular position determining section detects the angular position of said rotary body N times for each rotation, the clock rate of said clock signal generator of an apparatus for defining the location of a foreign object on a rotary body according to the invention may preferably be greater than M×N (Hz).

The position determining section of an apparatus for defining the location of a foreign object on a rotary body according to the invention may preferably start counting clock signals each time a new angular sector is detected by said angular position detecting section.

An apparatus according to the invention and having a configuration as described above determines that a foreign object is present on the rotary body whenever the output of the light receiving system exceeds a predetermined value and highly precisely defines the location of the detected foreign object in terms of a coordinate system by means of the output of the horizontal displacement detecting section, that of the angular position detecting section and the clock signal of the clock signal generator.

DETAILED DESCRIPTION OF THE PREFERRED EMBODIMENTS

Figure 1:
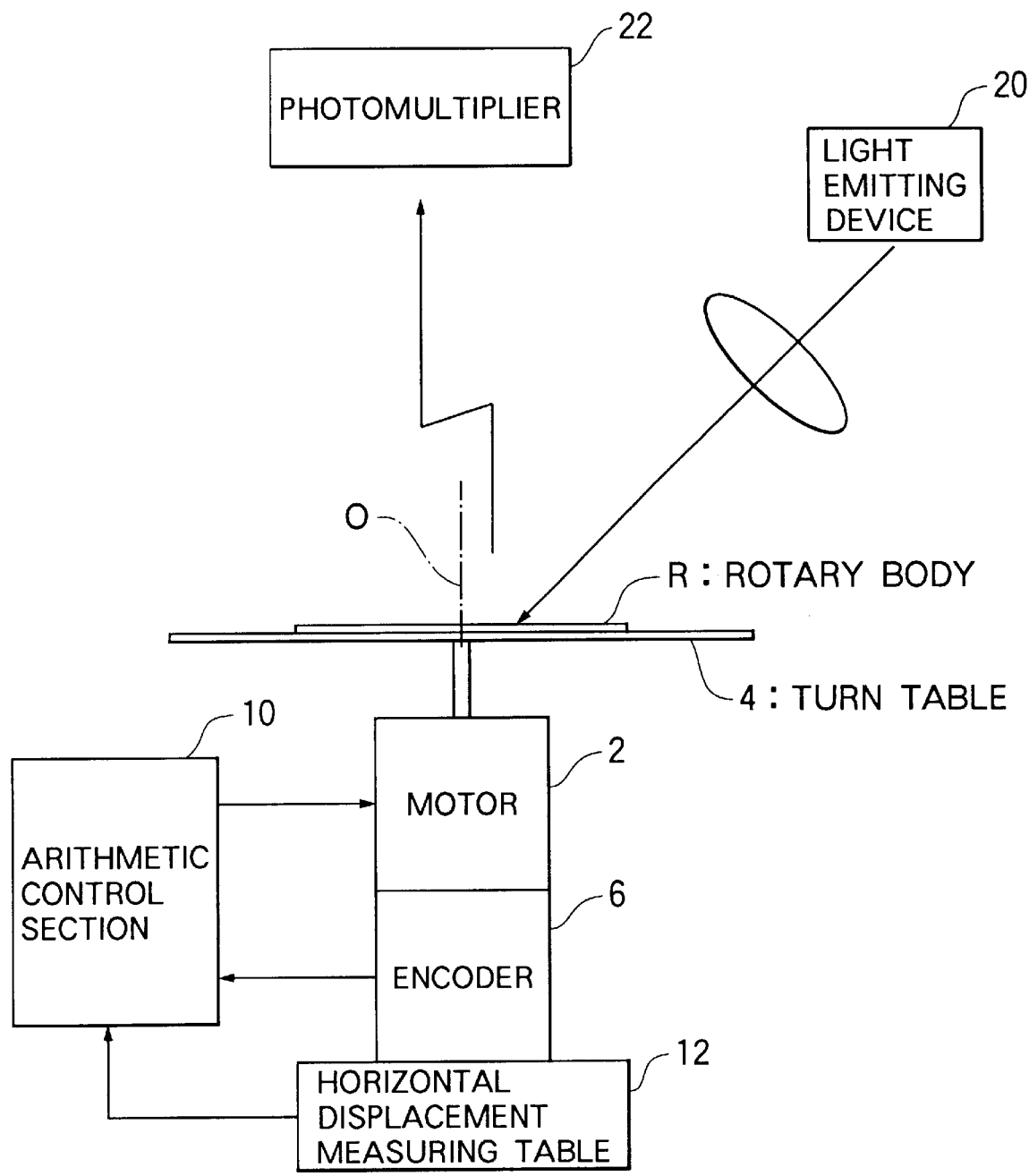
FIG. 1 is a schematic block diagram of a first embodiment of apparatus for defining the location of a foreign object on a rotary body according to the invention, showing its configuration.

Now, the present invention will be described in greater detail by referring to the accompanying drawings that illustrate preferred embodiments of the invention. Referring to FIG. 1 illustrating a first embodiment of the invention, it comprises a motor 2, a turn table 4 driven by the motor 2 to rotate around a vertical axis of rotation O and a rotary body R carried by the turn table 4 for examination. The rate of rotation of the turn table 4 is M, which may typically be 50 rotations per second. The motor 2 is combined with an encoder 6 that detects the rotary angle of the motor 2 and transmits a signal representing the detected rotary angle to an arithmetic control unit 10. The encoder 6 divides a full rotation of the turn table into a given number N, which may typically be 6,000. The angle of a full turn, or 360°, divided by that number is referred to as "an angular sector". The output of the arithmetic control unit 10 is applied to the motor 2, which in combination with the encoder 6 is placed on a horizontal displacement measuring table 12 so that the motor 2 and the encoder 6 may be horizontally moved and their horizontal displacement may be accurately measured. The signal representing the measured horizontal displacement is then transmitted to the arithmetic control unit 10.

Above the rotary body placed on the turn table 4 and offset from the axis of rotation O, there is provided a light emitting device 20 that emits a laser beam. There is also provided a photomultiplier 22 for detecting the quantity of light reflected by the rotary body R that is illuminated by the light emitting device 20.

Figure 2:
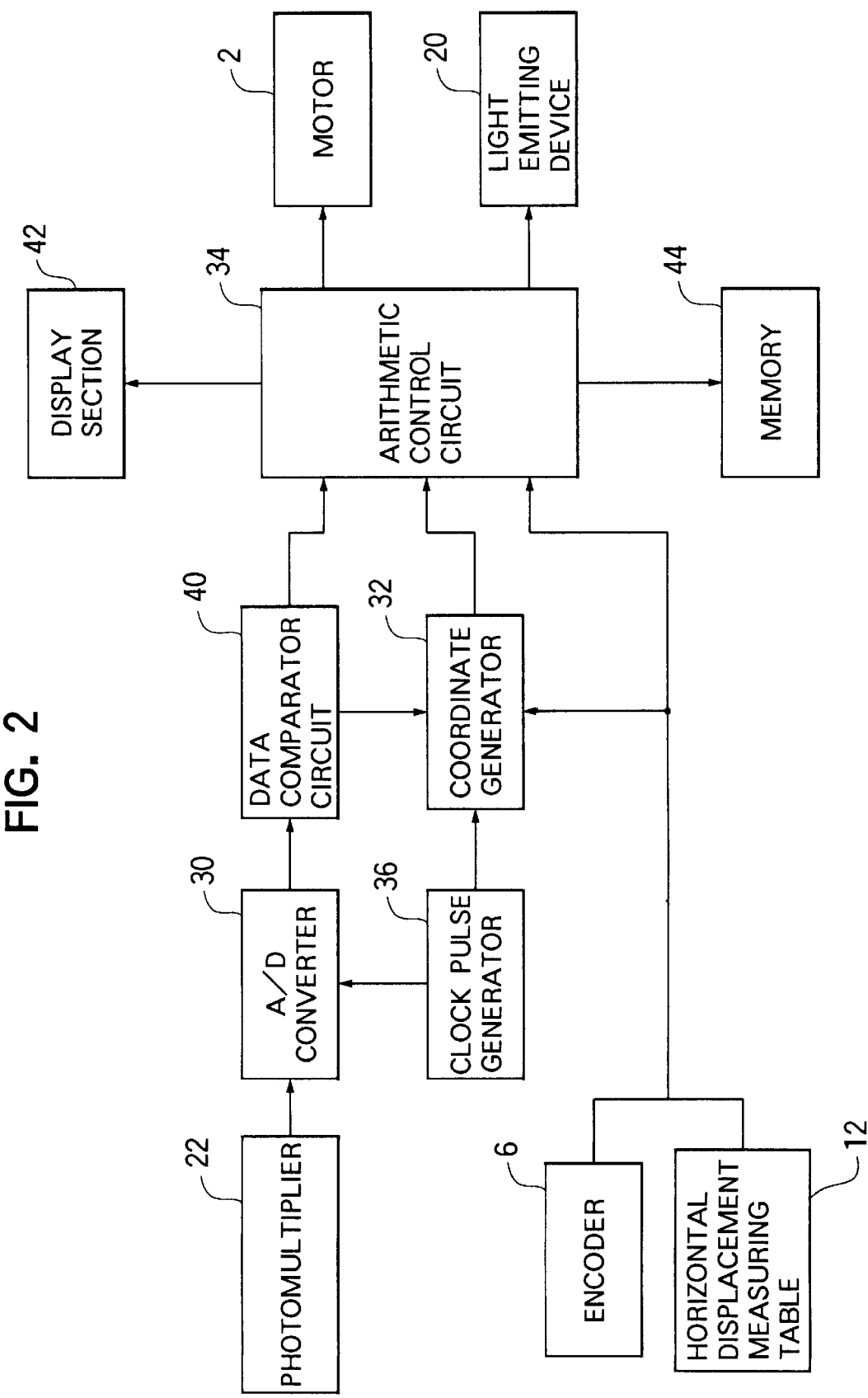
FIG. 2 is a block diagram illustrating the circuit configuration of the arithmetic control unit of the embodiment of FIG. 1.

Referring to the block diagram of FIG. 2, the output of the photomultiplier 22 is fed to an A/D converter 30 and the output of the encoder 6 and that of the horizontal displacement measuring table 12 are fed to a coordinate generator 32 and an arithmetic control circuit 34. The A/D converter 30 carries out an operation of analog-digital conversion for the output of the photomultiplier 22 in accordance with the timing of generating a clock pulse. The arithmetic processing operation of the arithmetic control circuit 34 will be described hereinafter. The output of a clock pulse generator 36 that generates a clock pulse independent of the output of the encoder 6 is applied to the A/D converter 30 and the coordinate generator 32, while the output of the A/D converter 30 is fed to the arithmetic control circuit 34 and the coordinate generator 32 via a data comparator circuit 40, which compares the existing maximum value with a value representing the data obtained by a new measurement cycle and sends out the whichever larger one. The output of the coordinate generator 32 and that of the data comparator circuit 40 are fed to the arithmetic control circuit 34.

The arithmetic control circuit 34 sends out a control signal to the motor 2 and the light emitting device 20 and an arithmetic signal to a display section 42 and a memory 44. The memory 44 stores the maximum quantity of light detected by the photomultiplier 22 for each angular sector and supplied by the arithmetic control circuit 34 along with the numerical values of the coordinates of each angular sector for that quantity. Alternatively, the memory 44 may be so arranged as to stores all the quantities of light detected by the photomultiplier 22 for each angular sector and the coordinates of each angular sector for the quantities.

The clock pulse generated by the clock pulse generator 36 is designed to have a frequency higher than that of the output of the encoder 6. For the above cited number of rotations M of the turn table 4 per unit time=50 rotations per second and numerical value N of the divisor for the encoder 6=6,000 for each full turn, the frequency of the output of the encoder 6=M×N=300 kHz.

Thus, the frequency of the clock pulse generated by the clock pulse generator 36 is set to a value greater than 300 kHz or typically between several MHz and tens of several MHz.

Figure 3:
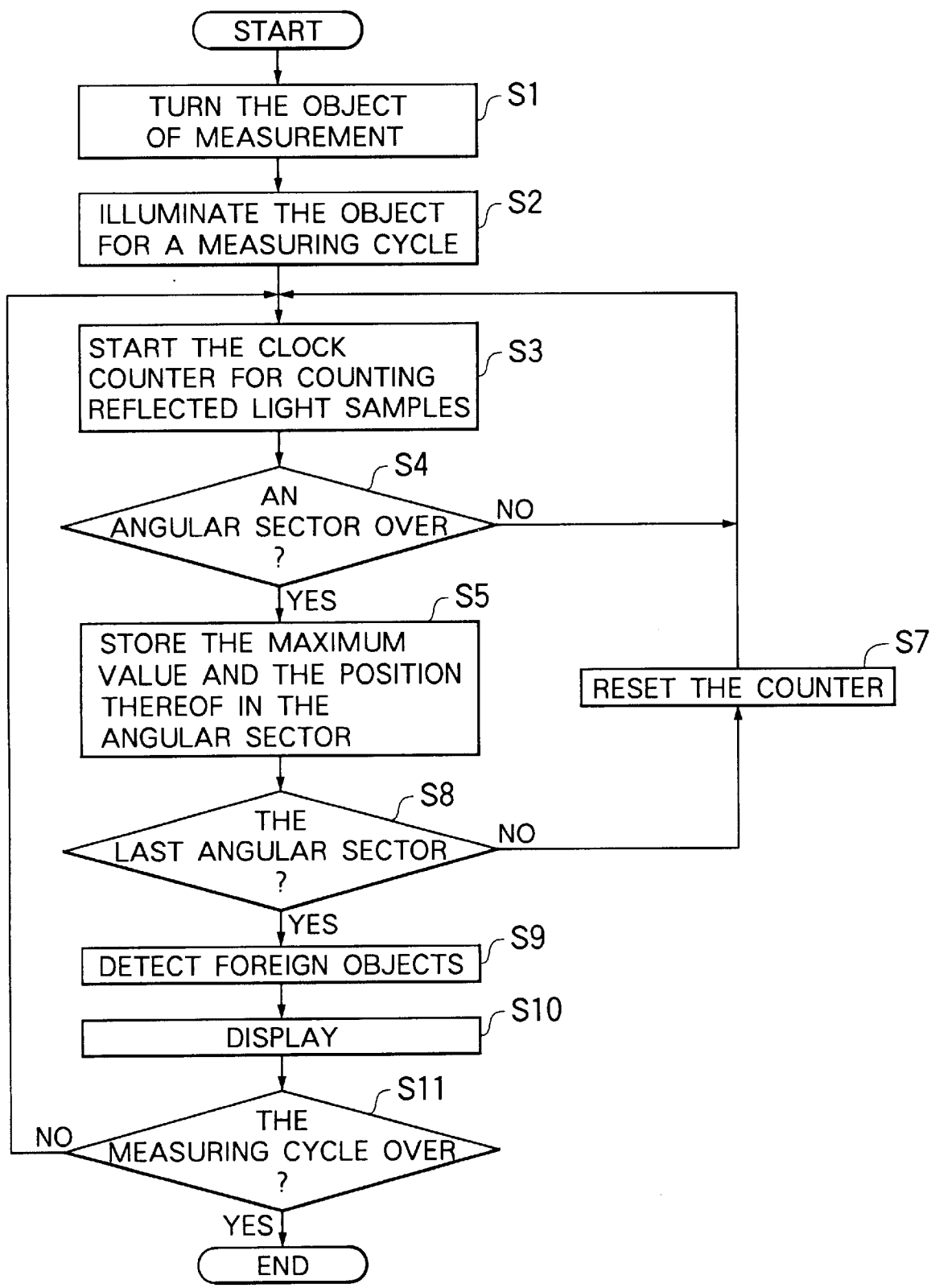
FIG. 3 is a flow chart of the operation of the arithmetic control unit of the embodiment of FIG. 1.

The rotary body R is typically divided into a number of coaxial zones and the operation of the arithmetic control circuit 34 of the first embodiment proceeds in a way as illustrated in the flow chart of FIG. 3 and described below for each coaxial zone.

In step S1, the turn table 4 is driven to rotate in order to rotate the rotary body R placed thereon.

In step S2, the light emitting device 20 is made to emit light to illuminate the rotary body R.

In step S3, the quantity of light received by the photomultiplier 22 for an angular sector is read along with the coordinates for that quantity and this reading operation is repeated for a given number of times.

In step S4, if the quantities of light of all the specified positions in that angular sector received by the photomultiplier 22 and the coordinates for the quantities have been read or not is determined. If not, the operation returns to step S3.

If, to the contrary, the answer to the question in step S4 is affirmative, the operation proceeds to step S5, where the maximum quantity of light received by the photomultiplier 22 for that angular sector and the coordinates for the maximum quantity are stored in the memory 44.

In step S8, if the current angular sector is the last one of all the angular sectors for a full turn or not is determined.

If it is determined in step S8 that the current angular sector is not the last one of all the angular sectors for a full turn, the clock pulse counter (not shown) is reset in step S7 and the operation goes back to step S3.

If, to the contrary, it is determined in step S8 that the current angular sector is the last one of all the angular sectors for a full turn, the operation proceeds to step S9, where it is determined if the maximum quantity of light of each of the angular sectors is greater than a predetermined value or not and any maximum quantities that exceed the predetermined value are regarded as so may foreign objects.

Then, in step S10, the angular sectors of the foreign objects detected in step S9 and their coordinates are displayed on the display section.

In step S11, it is determined if the operation of the current measuring cycle is over or not. If not, the operation goes back to step S3 and typically the above procedures are repeated for a next coaxial zone that is not covered by the above operation.

Figure 5:
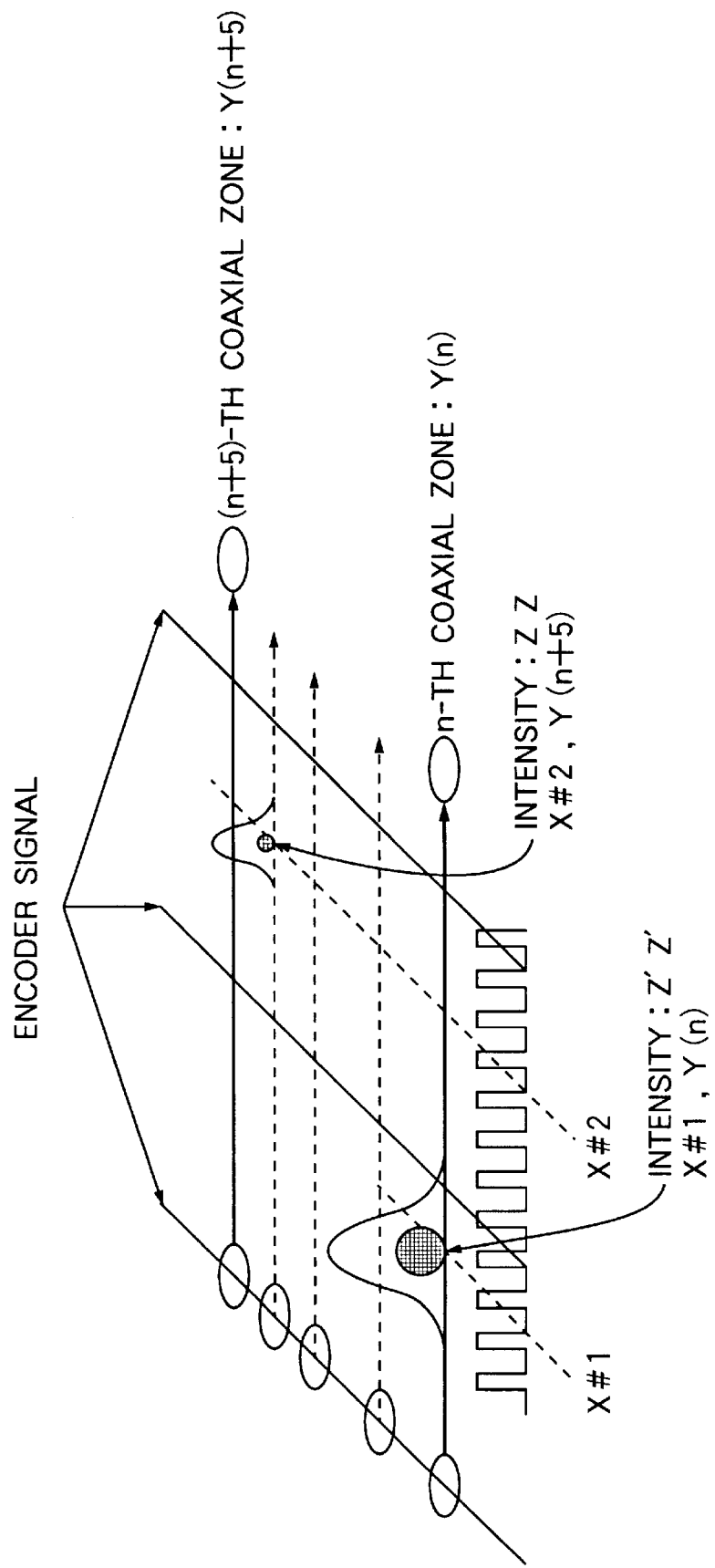
FIG. 5 is a schematic conceptual diagram of the operation of a memory that can be used for the purpose of the present invention.

In the memory 44 for storing the outcome of the operation of the arithmetic control circuit 34 of the first embodiment, data on the detected foreign objects are stored in terms of time (X-axis), coaxial zone (Y-axis) and maximum quantity of received light (Z-axis) as schematically illustrated in FIG. 5. Thus, foreign objects having respective intensities Z Z, Z' Z' are located in the n-th coaxial zone and the (n+5)-th coaxial zone respectively.

Figure 4:
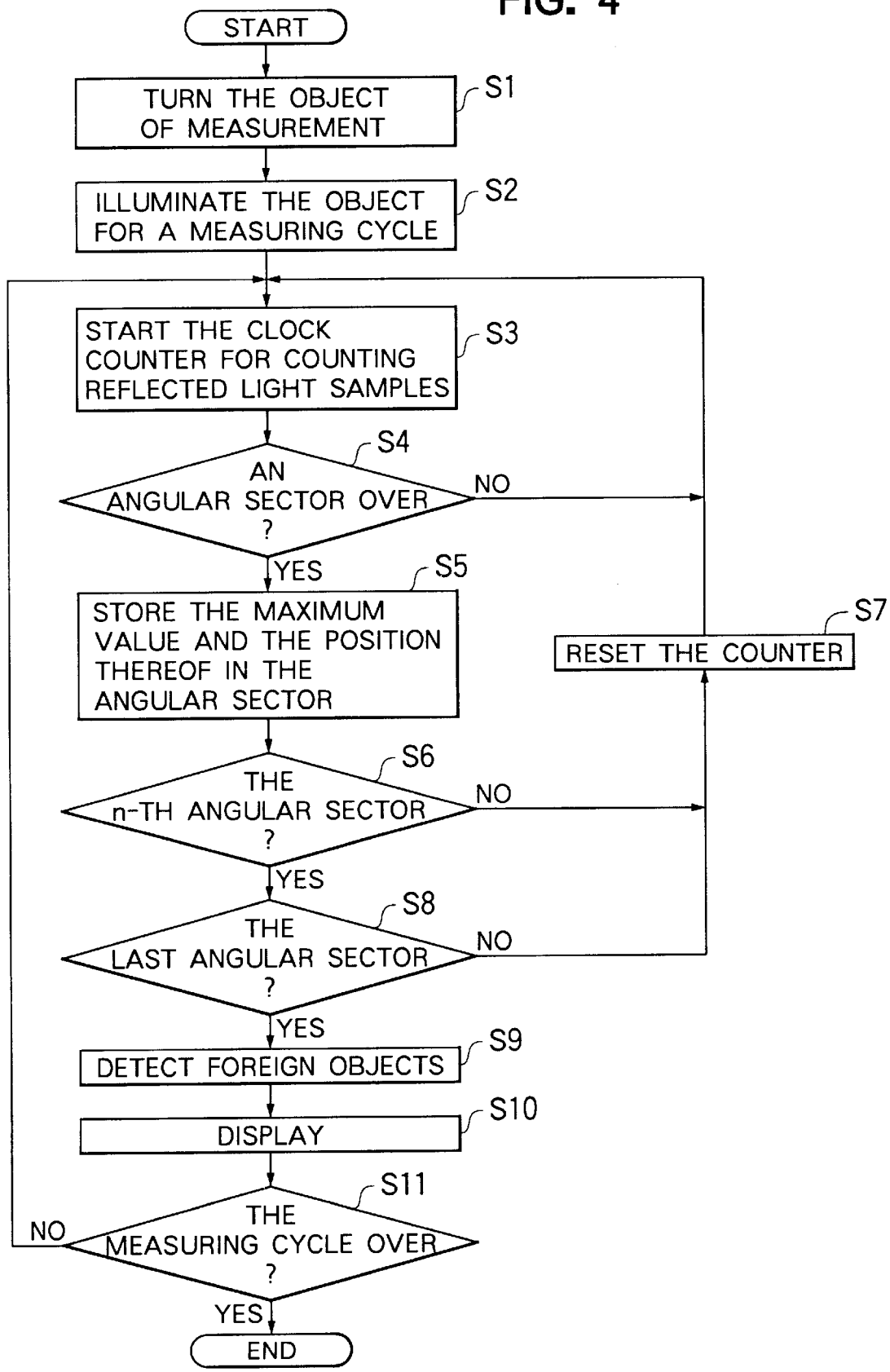
FIG. 4 is a flow chart of the operation of the arithmetic control unit of a second embodiment of the invention.

FIG. 4 is a flow chart of the operation of the arithmetic control circuit 34 of the second embodiment. In FIG. 4, the steps of operation same as those of the arithmetic control circuit 34 of the first embodiment are respectively denoted by the same step numbers and will not be described here any further.

In step S6, it is determined if the operation from step S3 through step S5 is completed or not for the n-th angular sector (n=integer greater than 1).

If it is determined in step S6 that the operation for the n-th angular sector is not completed, the operation proceeds to step S7 to reset the clock pulse counter (not shown) and returns to step S3. If it is determined in step S6 that the operation for the n-th angular sector is completed, the operation proceeds to step S8.

[ADVANTAGES OF THE INVENTION]

As described above in detail, an apparatus for defining the location of a foreign object on a rotary body in terms of a coordinate system according to the invention is simple in circuit configuration, can be manufactured at low cost and yet operates accurately for detecting a foreign object.

If the clock rate of the clock signal generator is made greater than the frequency of the output of the angular position detecting section of an apparatus for defining the location of a foreign object on a rotary body in terms of a coordinate system according to the invention, the coordinates of the detected foreign object can be defined more finely than those of the angular sectors used for the apparatus.

If the position determining section of an apparatus for defining the location of a foreign object on a rotary body in terms of a coordinate system according to the invention is so arranged as to start counting clock signals each time a new angular sector is detected by the angular position detecting section, the apparatus is free from the problem of accumulating timing errors of clock pulse in the angular position detecting device.

What is claimed is:

1. An apparatus for defining a location of a foreign object on a rotary body in terms of a coordinate system, the rotary body adapted to rotate around a horizontally-movable vertical axis of rotation, the apparatus comprising:
   a) horizontal displacement detecting means for detecting a horizontal displacement of the vertical axis and for transmitting a first signal representing the horizontal displacement;
   b) angular position detecting means for detecting an angular position of the rotary body and for providing a second signal representing the angular position;
   c) lighting optical means for illuminating the rotary body's surface;
   d) light receiving means for receiving light that is reflected by the rotary body's surface and for producing a third signal representing reflected light;
   e) clock signal generating means for generating a clock signal;
   f) representative value determining means, responsive to the second signal representing the angular position, for determining that a maximum value of the third signal corresponds to a representative value of angular position;
   g) position determining means for determining a position corresponding to the representative value, based on:
      1) the first signal representing the horizontal displacement;
      2) the second signal representing the angular position; and
      3) the clock signal;
   wherein the position determining means starts counting clock signals each time a new angular sector is detected by the angular position detecting means; and
   h) foreign object detecting means for determining that a representative value exceeding a predetermined level corresponds to the foreign object.

2. The apparatus of claim 1, wherein:
   if a) and b):
      a) the rotary body rotates at a rate of M rotations per second; and
      b) the angular position determining means detects the angular position of the rotary body N times per rotation;
   then:
      c) the clock signal generating means operates at a clock rate that is greater than a mathematical product M times N cycles per second.

\* \* \* \* \*